(12) United States Patent
Okamoto et al.

(10) Patent No.: US 10,106,691 B2
(45) Date of Patent: Oct. 23, 2018

(54) METAL PASTE FOR GAS SENSOR ELECTRODE FORMATION

(71) Applicant: Tanaka Kikinzoku Kogyo K.K., Tokyo (JP)

(72) Inventors: Nobuhisa Okamoto, Hiratsuka (JP); Takuya Hosoi, Hiratsuka (JP); Nobuyuki Akiyama, Hiratsuka (JP); Akihiro Nakai, Hiratsuka (JP); Shigekazu Onozumi, Hiratsuka (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 15/661,886

(22) Filed: Jul. 27, 2017

(65) Prior Publication Data

US 2017/0328860 A1 Nov. 16, 2017

Related U.S. Application Data

(63) Continuation of application No. 14/762,374, filed as application No. PCT/JP2014/051629 on Jan. 27, 2014, now Pat. No. 9,758,680.

(30) Foreign Application Priority Data

Jan. 28, 2013 (JP) .................................. 2013-012923
Aug. 28, 2013 (JP) .................................. 2013-176786

(51) Int. Cl.
  *C09D 5/24* (2006.01)
  *G01N 27/407* (2006.01)
  (Continued)

(52) U.S. Cl.
  CPC .............. *C09D 5/24* (2013.01); *C04B 35/482* (2013.01); *C09D 1/00* (2013.01); *C09D 7/20* (2018.01);
  (Continued)

(58) Field of Classification Search
  None
  See application file for complete search history.

(56) References Cited

U.S. PATENT DOCUMENTS 5,626,923 A * 5/1997 Fitzgibbons ............ C03C 1/008
                                                    427/299
2003/0026961 A1   2/2003 De La Prieta et al.
(Continued)

FOREIGN PATENT DOCUMENTS

JP    2005-133114 A    5/2005
JP    2005-283240 A    10/2005
(Continued)

OTHER PUBLICATIONS

PCT, International Search Report PCT/JP2014/051629, dated Apr. 22, 2014.

*Primary Examiner* — Katie L Hammer
(74) *Attorney, Agent, or Firm* — Orrick, Herrington & Sutcliffe LLP; Joseph A. Calvaruso

(57) ABSTRACT

To be provided is a metal paste from which an electrode having high electrode activity as a sensor electrode of various gas sensors can be produced. The present invention is a metal paste for forming a gas sensor electrode obtained by dispersing a conductive particle including Pt or a Pt alloy and a ceramic powder including zirconia or stabilized zirconia, or any of zirconia and stabilized zirconia and one or more oxides of La, Ce, Pr, Nd, Sm, and Hf in a solvent, the metal paste further including an inorganic oxide particle containing alumina and an insoluble particle that is insoluble in the solvent, in which 0.5 or more to 3.0 mass % or less of the inorganic oxide particle and 1.0 to 5.0 mass % of the insoluble particle are dispersed based on the mass of the solid content of the conductive particle, the ceramic powder, the inorganic oxide particle, and the insoluble particle.

18 Claims, 2 Drawing Sheets

(51) Int. Cl.
*C04B 35/482* (2006.01)
*C09D 1/00* (2006.01)
*H01B 1/16* (2006.01)
*C09D 7/20* (2018.01)
*H01B 1/02* (2006.01)

(52) U.S. Cl.
CPC ..... *G01N 27/4073* (2013.01); *G01N 27/4075* (2013.01); *H01B 1/02* (2013.01); *H01B 1/16* (2013.01); *B22F 2301/25* (2013.01); *C04B 2235/3217* (2013.01); *C04B 2235/3225* (2013.01); *C04B 2235/408* (2013.01)

(56) References Cited

U.S. PATENT DOCUMENTS

| | | |
|---|---|---|
| 2003/0230484 A1 | 12/2003 | Jain et al. |
| 2005/0241136 A1* | 11/2005 | Wu .................... G01N 27/4077 29/592.1 |
| 2006/0231397 A1 | 10/2006 | Nakagaki et al. |
| 2012/0217160 A1 | 8/2012 | Hayashi et al. |
| 2014/0311906 A1 | 10/2014 | Oya et al. |

FOREIGN PATENT DOCUMENTS

| | | |
|---|---|---|
| JP | 2008-164411 A | 7/2008 |
| JP | 2009-289679 A | 12/2009 |
| JP | 2010-256129 A | 11/2010 |
| JP | 4834170 B1 | 12/2011 |

* cited by examiner

TEST No. 3                    TEST No. 14

METAL PASTE FOR GAS SENSOR ELECTRODE FORMATION

CROSS REFERENCE TO RELATED APPLICATIONS

This application is a continuation of and claims priority to co-pending U.S. patent application Ser. No. 14/762,374, which was filed Jul. 21, 2015 and claimed priority to International Patent Application Number PCT/JP2014/051629, which was filed on Jan. 27, 2014 and claimed priority to Japanese Patent Application Number 2013/176786, which was filed on Aug. 28, 2013 and Japanese Patent Application Number 2013/012923, which was filed on Jan. 28, 2013. The disclosure of the patent applications are herein incorporated by reference in their entirety and for all purposes.

TECHNICAL FIELD

The present invention relates to a metal paste for producing a sensor electrode configuring a sensing portion of a gas sensor such as an oxygen sensor or a NOx sensor.

BACKGROUND ART

As an electrode configuring a sensor electrode or a heater electrode for various gas sensors such as an oxygen sensor, a NOx sensor, and an exhaust gas temperature sensor, one obtained by calcination of a metal paste has been used hitherto. The reason why a metal paste is used in producing of these electrodes is that the metal paste can cope with a complicated pattern of an electrode, and further, that applying and calcining the metal paste on a green sheet forming a ceramic substrate allows a substrate and an electrode to be produced simultaneously, which is preferable from the viewpoint of production efficiency.

As the configuration of the metal paste for forming an electrode, a mixture of a conductive particle such as a precious metal and a ceramic powder such as $Al_2O_3$ and $ZrO_2$ with a solvent is known. The reason for mixing a ceramic powder with a metal paste is to improve adhesion of an electrode, when the metal paste is applied and calcined on a green sheet to simultaneously produce a substrate and an electrode as described above, with a difference in shrinkage rate between the metal paste and the green sheet corrected to solve problems for warpage and deformation of the substrate. In addition, the ceramic powder secures moldability of an electrode film. On the other hand, there is also a disadvantage in that the ceramic powder increases a resistance value of an electrode film to be produced and is likely to make the resistance value higher than in an electrode of a bulk metal. Therefore, regarding the use of the ceramic powder, searching for an optimal usage type or mixing amount is a matter to be considered while taking into account a balance between the securing of moldability and the reducing of resistance.

Regarding the matter to be considered, the present inventors disclose a metal paste from which an electrode film of low resistance can be produced and which is excellent in adhesion and conformability to a substrate, and an electrode produced by using the same (Patent Document 1). In the metal paste suggested by the present inventors, as the configuration of a conductive particle, a conductive particle having a core/shell structure is used in which a ceramic powder is bonded and coated on an outer surface of a core particle including a precious metal. Further, when the conductive particle has a core/shell structure, an electrode of low resistance is formed by dispersion of the ceramic powder in a fine state in a process of sintering the metal paste and suppression of the coarsening of the ceramic powder that is a factor of increasing the resistance.

RELATED ART DOCUMENT

Patent Document

Patent Document 1: Japanese Patent No. 4834170

SUMMARY OF THE INVENTION

Problems to be Solved by the Invention

An electrode formed from the metal paste suggested by the present inventors exhibits desired characteristics in application for a lead wire, a heater electrode, or the like and the usability thereof is confirmed. However, as a result of the present inventors' studies, it is confirmed that the electrode is difficult to exert sufficient performance as a sensor electrode serving as a sensing portion of various gas sensors. In a sensor electrode of the gas sensors, electrode activity according to types of gas that is a measurement target in a test gas is required. However, an electrode formed from a conventional metal paste is inferior in this electrode activity.

In this regard, the present invention is to provide a metal paste from which an electrode having a sufficient electrode activity as a sensor electrode for various gas sensors can be formed.

Means for Solving the Problems

In order to solve the aforementioned problem, the present inventors first reexamined a preferred configuration of a sensor electrode of a gas sensor. FIG. 1 is a diagram for describing a configuration of an oxygen sensor as a general gas sensor. In FIG. 1, a sensing portion of the gas sensor is set in a solid electrolyte interposed between anode and cathode sensor electrodes. In gas analysis using the gas sensor, a measurement gas (oxygen) introduced to the cathode electrode passes through the inside of the electrode to reach the solid electrolyte. At this time, oxygen molecules are converted into ions by action of a conductive metal particle phase (platinum or the like) in the cathode electrode, the ions pass through the solid electrolyte, and then the oxygen concentration is detected based on a current change caused thereby. In this measurement process, reaction for detecting oxygen molecules occurs in a three-phase interface which the conductive metal, the solid electrolyte, and the measurement gas share (FIG. 2).

Therefore, it can be said that the electrode activity of the sensor electrode depends on an amount of formation of the three-phase interface in the electrode. In this regard, in order to sufficiently form the three-phase interface in the electrode, it is an option to make the configuration of the electrode porous. Here, when the metal paste having a core/shell structure suggested by the present inventors described above is considered, an electrode formed from this metal paste has low resistance, but the porous property thereof is not considered. The electrode is formed relatively densely. On the contrary, when it assumed that this electrode is used as a sensor electrode, this densified state becomes drawback and thus the three-phase interface is not sufficiently formed in the electrode. According to this, it is considered that the electrode activity may not be obtained.

However, it does not mean that the sensor electrode be simply porous, but it is premised on that the sensor electrode requires electric conductivity (to have low resistance) for acting as a conductive body. In this regard, compatibility between this electric conductivity and the porous property are difficult to be achieved. In the case of aiming at only the porous property of the electrode, the object can be achieved by using a general metal paste obtained by mixing a conductive particle and a ceramic powder. For example, in a general metal paste, when the particle diameter of the conductive particle is increased, the configuration of the electrode can be adjusted to be porous. However, in this case, since the conductive metal is excessively coarsened after calcination, a gap between the conductive metals is increased and thus a resistance value is considerably increased. In such a metal paste containing a conductive particle having a large particle diameter, conductivity is not obtained until the film thickness of the electrode is increased. When the film thickness of the electrode is increased, a sensor element is increased in size and a used amount of a metal (a precious metal such as platinum) is also increased, which is adverse in terms of cost. As described above, it is not easy to adjust the configuration of the electrode while the electric conductivity of the electrode is secured.

The present inventors conducted intensive studies on a metal paste capable of suppressing the coarsening of the conductive particle while having a porous structure favorable for a sensor electrode. Then, the present inventors have conceived the present invention by using a metal paste having a general configuration, which is obtained by mixture and dispersion of a conductive particle and a ceramic powder in a solvent, without using a conductive particle having a core/shell structure in which an electrode may be densified, and by adding both of an inorganic oxide particle having an effect of suppressing the sintering of a conductive particle and an insoluble particle used for forming pores in an electrode after calcination to the metal paste.

That is, the present invention is a metal paste for forming a gas sensor electrode, the metal paste being obtained by dispersing a conductive particle including Pt or a Pt alloy and a ceramic powder including zirconia or stabilized zirconia, or any of zirconia and stabilized zirconia and one or more oxides of La, Ce, Pr, Nd, Sm, and Hf in a solvent, the metal paste further including: an inorganic oxide particle including alumina and an insoluble particle that is insoluble in the solvent, wherein 0.5 to 3.0 mass % of the inorganic oxide particle and 1.0 to 5.0 mass % of the insoluble particle are dispersed based on mass of solid content of the conductive particle, the ceramic powder, the inorganic oxide particle, and the insoluble particle.

Hereinafter, the configuration of the present invention will be described in more detail. As described above, a metal paste for forming a gas sensor electrode according to the present invention is one obtained in a metal paste obtained by mixing and dispersing a conductive particle and a ceramic powder in a solvent is basically used and both of an inorganic oxide particle and an insoluble particle are added to the metal paste. Incidentally, as described above, in the present invention, as a basis for defining the contents of the conductive particle, the ceramic powder, the inorganic oxide particle, and the insoluble particle, the total mass of solid contents thereof is used.

The conductive particle includes Pt or a Pt alloy. Theses metals have favorable conductivity, and also are excellent in heat resistance or corrosion resistance. Since some of various sensors such as an exhaust sensor for an automobile may be used under high temperature, these metals are suitable for an electrode material for such sensors. Whether to use Pt or the Pt alloy as the conductive particle can be determined depending on the use and the demanded characteristics of the conductive particle. Pt has lower resistance than a Pt alloy, and thus is suitable for an electrode in which low resistance is primarily required. On the other hand, although a Pt alloy has higher resistance than Pt, it is low in a temperature coefficient of resistance (TCR) and thus suitable for an electrode in which a low TCR is required.

Further, when a Pt alloy is used, Pd, Au, Ag, and Rh are preferable as a metal alloyed with Pt. In addition, a Pt—Pd alloy including Pd is preferable in that it has good compatibility with ceramic serving as a substrate and in that it also shows good wettability when being converted into a paste. Incidentally, the content of Pd in a Pt—Pd alloy is preferably 30 mass % or less. This is because if the content of Pd is too high, a Pd oxide is likely deposited in the process of calcining, and thus the reliability of an electrode is decreased.

The particle diameter of the conductive particle is preferably 5 nm to 2 µm. When the particle diameter thereof is less than 5 nm, the conductive particle is inferior in dispersibility and thus a homogeneous metal paste is difficult to be produced. In addition, when the particle diameter of the conductive particle exceeds 2 µm, it is likely to form a coarse particle even in the presence of the inorganic oxide particle that is added as a sintering suppressing agent, and tends to raise resistance of an electrode. Incidentally, the mixing amount of the conductive particle is preferably 72 to 88.5 mass % based on the mass of the solid content.

The ceramic powder exhibits the same action as that of a conventional metal paste, and is an essential component that is used to correct a difference in shrinkage rate between a metal paste and a substrate to improve adhesion, thereby securing moldability of an electrode. As this ceramic powder, ceramic containing zirconia ($ZrO_2$) is applicable. Specific examples thereof include stabilized zirconia added with several percentage of an oxide such as yttria or calcia, in addition to pure zirconia. When stabilized zirconia is used, the mixing amount of yttria or the like is not particularly limited, and partially-stabilized zirconia may be used. Incidentally, since it is preferable that the ceramic powder of the metal paste be the same material as ceramic which is generally used in a substrate to be coated, ceramic (oxides of La, Ce, Pr, Nd, Sm, Hf, and the like) having oxide ion conductivity other than $ZrO_2$ may be contained.

In the sensor electrode according to the invention, the dispersed amount (content) of the ceramic powder is preferably 10 to 20 mass % based on the mass of the solid content. When the amount thereof is less than 10 mass %, intrisic action (conformability to a shrinkage rate of a substrate) thereof is difficult to be exerted, and such an amount is an insufficient amount as a skeleton in order to obtain a porous structure of an electrode. On the other hand, when the amount of the ceramic powder exceeds 20 mass %, a proximity state to a conductive metal at the inside of the electrode is difficult to be obtained and thus resistance is increased. Accordingly, there is a concern that the sensor electrode may lose a function as an electrode. Further, the particle diameter of the ceramic powder is preferably 100 to 500 nm. This is because a coarse ceramic powder inhibits dispersion of the conductive particle in the electrode. In addition, since the ceramic powder acts as a skeleton of an electrode, a ceramic powder having an excessively fine particle diameter has an influence on porous properties of the electrode.

Further, the metal paste according to the present invention is an inorganic oxide particle and an insoluble particle being added together with the conductive particle and the ceramic powder described above.

The inorganic oxide particle is added for the purpose of suppressing the sintering of the conductive particle and preventing the conductive particle from coarsening. The coarsening of the conductive particle has an influence on resistance of the electrode. That is, for this reason, the inorganic oxide particle is added to lower resistance of the electrode. The inorganic oxide particle used as a sintering suppressing agent for the conductive particle includes alumina ($Al_2O_3$). According to the present inventors, an inorganic oxide including alumina can inhibit conductive particles from being sintered to each other in the paste in the process of calcining.

The added amount of the inorganic oxide particle needs to be 0.5 to 3.0 mass % based on the mass of the solid content. When the added amount thereof is less than 0.5 mass %, an effect of suppressing the sintering of the conductive particle is not sufficient. In addition, when the added amount thereof exceeds 3.0 mass %, conductivity of oxide ions is inhibited, which is not favorable.

Further, the particle diameter of the inorganic oxide particle is preferably 5 to 500 nm. When the particle diameter thereof is less than 5 nm, the inorganic oxide particle is difficult to be uniformly dispersed in the paste, and thus there is a concern that the conductive particle is locally coarsened. In addition, since the inorganic oxide particle is also sintered in the process of calcining, an inorganic oxide particle having a large particle diameter is coarsened and thus the effect of suppressing the sintering of the conductive particle cannot be uniformly exerted. For this reason, an upper limit of the particle diameter is preferably 500 nm. Even when the particle diameter of the inorganic oxide particle is either too small or too large, there is a possibility that the inorganic oxide particle does not sufficiently function in consideration of the action of the inorganic oxide particle in the present invention.

Next, the insoluble particle that is another feature of the present invention will be described. The term "insoluble" means a state where a substance is undissolved in a solvent in which each component of the metal paste is mixed and dispersed. The "insoluble particle" in the present invention is a particle having a property in which the particle is burnt down at high temperature. The insoluble particle is dispersed in the metal paste in a solid state and this solid state is maintained even after the insoluble particle is applied on a substrate, but the insoluble particle is burnt down in the process of calcining (about 1300 to 1600° C.) when an electrode is formed. Therefore, in the electrode after calcination, pores are formed on a portion of the electrode where the insoluble particle is present. With such an action, a porous structure is imparted to the electrode to form a three-phase interface for improvement of the electrode activity. That is, the insoluble particle is added as a factor for improvement of the electrode activity to the metal paste.

As primary specific examples of the insoluble particle, organic substances such as acryl, polyethylene, polyethylene terephthalate, polycarbonate, fluorine resin, and theobromine can be cited. This is because these substances are insoluble in a solvent generally used in a metal paste, and can be burnt down at high temperature. When these organic substances are used, the added amount is 1.0 to 5.0 mass % based on the mass of the solid content. When the added amount is less than 1.0 mass %, sufficient pores cannot be formed. On the other hand, when the added amount exceeds 5.0 mass %, the thickness of the calcined film becomes thinner, and thus there is a tendency that a required film thickness is difficult to be achieved.

As the insoluble particle, in addition to the organic substances described above, carbon, diamond powder, and the like are applicable. This is because carbon or diamond powder is insoluble in a solvent generally used in a metal paste and can be burnt down at high temperature. As carbon in the present invention, in addition to an amorphous carbon substance such as carbon black, graphite having a layer structure, and the like are also applicable. Regarding the added amount of the insoluble particle, in the case of using the organic substance, the added amount is 1.0 to 5.0 mass % as described above. On the other hand, in the case of using carbon or diamond powder, the added amount can be set to 1.0 to 15.0 mass %. In addition, in the case of using carbon or diamond powder, the added amount is preferably 5.0 to 15.0 mass %. Although it is possible to impart a porous structure even when the added amount is less than 5.0 mass %, it is easy to obtain an electrode having particularly preferable conductivity and electrode activity when the added amount is 5.0 mass % or more. When the added amount exceeds 15.0 mass %, there is a tendency that conductivity and electrode activity are decreased.

The particle diameter of the insoluble particle is preferably 0.5 to 3 μm. This is because, when the particle diameter thereof is less than 0.5 μm, pores are too small and thus gas cannot be sufficiently diffused, and when the particle diameter thereof exceeds 3 μm, pores are too large and thus the distribution of fine pores in the whole film is not sufficient.

In the present invention, it is necessary to add both of the inorganic oxide particle and the insoluble particle. When only one of the inorganic oxide particle and the insoluble particle is added, the effect in the present invention is not exerted. This is because both additives have different mechanisms from each other and thus different effects (an effect of suppressing the coarsening of the conductive particle and an effect of making an electrode structure porous) are exerted.

The metal paste according to the present invention is one obtained by dispersing the conductive particle, the ceramic powder, the inorganic oxide particle, and the insoluble particle described above in a solvent. Here, as a solvent which is applicable to the producing of the metal paste in the present invention, conventionally used solvents can be used. Specifically, common solvents such as ethylene glycol, propylene glycol, ethylene glycol monophenyl ether, benzyl alcohol, kerosene, paraffin, γ-butyrolactone, N-methyl pyrrolidone, butyl carbitol, turpentine oil, α-terpineol, and terpineol are applicable.

In the metal paste, regarding the mixing amount of the solvent and the solid content (the conductive particle, the ceramic powder, the inorganic oxide particle, and the insoluble particle), the solid content is preferably 50 to 90 mass % with respect to the whole paste. This is because, if the amount is less than 50 mass %, an electrode film becomes too thin, and if the amount exceeds 90 mass %, it makes it difficult to prepare a paste.

Further, a resin usually used may be added to the metal paste in order to allow the metal paste to have viscosity and thixotropy. This resin is usually natural resins, amino-based resins, alkyd resins and the like. In particular, a resin such as ethyl cellulose is preferable.

The metal paste according to the present invention can be produced by mixing the conductive particle, the ceramic powder, the inorganic oxide particle, and the insoluble particle with the solvent. At this time, each powder of the conductive particle, the ceramic powder, the inorganic oxide particle, and the insoluble particle may be mixed in advance and the mixed powder may be dispersed in the solvent, or each powder may be added and dispersed sequentially into the solvent. In the mixing of the solvent and the solid contents, it is preferable that mixing and kneading be sufficiently performed by a three-roll mill or the like in order to achieve uniformity.

In a case where an electrode is produced by using the metal paste according to the present invention, the calcination temperature is preferably 1300 to 1600° C. This is because an electrode having a low resistance value can be obtained by sufficient sintering. An electrode film to be formed in this way is in a state that fine particles are dispersed and has a porous structure with appropriate pores.

Advantageous Effects of the Invention

As described above, when the metal paste for forming a sensor electrode according to the present invention is used, it is possible to form an electrode having activity and conductivity favorable in application as a gas sensor electrode. In this electrode, an appropriately fine conductive particle and the ceramic powder are dispersed while the electrode has a porous structure appropriately including a three-phase interface that is necessary as a reactive site, and a resistance value is low while the electrode has high activity.

DESCRIPTION OF EMBODIMENTS

Figure 1:
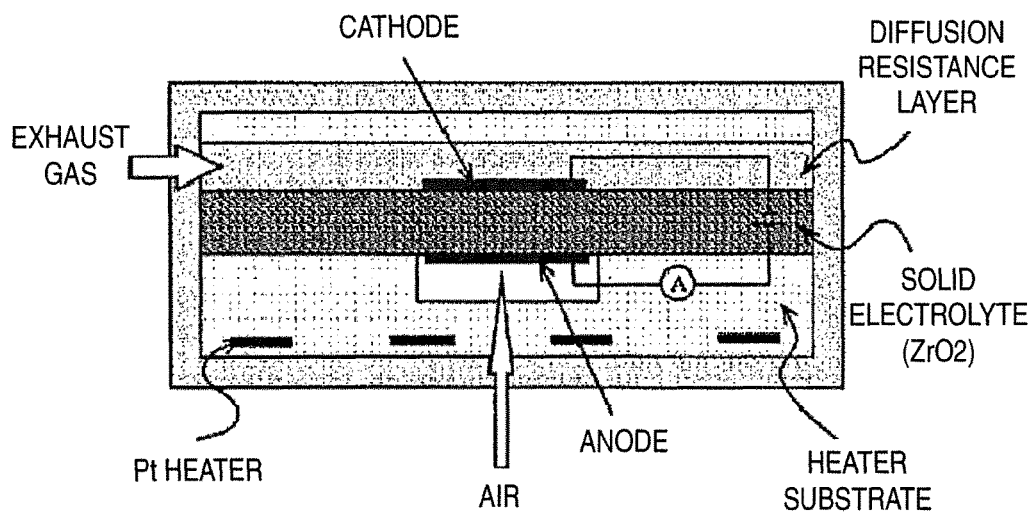
FIG. 1 is a diagram for describing the configuration of a general oxygen sensor.
Figure 2:
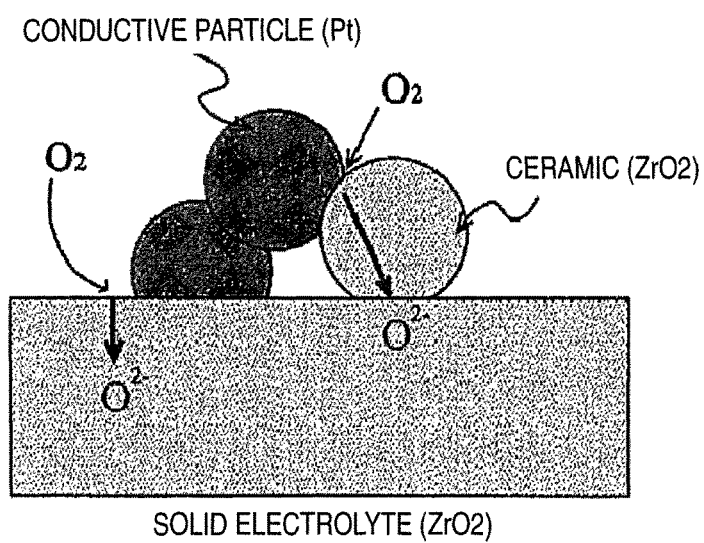
FIG. 2 is a diagram for describing the inside (three-phase interface) of an electrode of an oxygen sensor.

Hereinafter, an embodiment of the present invention will be described. In this embodiment, metal pastes were produced in 63 wt % of Pt (a particle diameter of 0.7 μm) used as a conductive particle, 15 wt % (8 mol) of YSZ (yttria-stabilized zirconia: a particle diameter of 0.2 μm) was used as a ceramic powder, and further, various inorganic oxide particles and insoluble particles each having a different particle diameter were mixed. Incidentally, diamond used as an insoluble particle was MD800 produced by Tomei Diamond Co., Ltd. and graphite was SGP-3 produced by SEC Carbon Ltd. Then, these metal pastes were applied to substrates and then calcined to form electrodes. Electrical characteristics of these electrodes were evaluated.

The metal paste was produced as follows. Each powder was mixed and then placed in terpineol as a solvent. Further, a diamine-based surfactant and ethyl cellulose were added thereto, followed by being mixed and kneaded in a three-roll mill to form a paste. The mixing amount of the mixed powder was 80 mass % with respect to the whole paste.

After the metal paste was produced, an electrode was formed and evaluated. The electrode was formed by applying the metal paste on a 99 mass % YSZ green sheet (a thickness of 0.3 mm) by screen printing. Thereafter, the resultant was calcined at 1450° C. for 1 hour to form an electrode. The electrode was produced such that the dimension thereof after calcination would be 2 mm×4 mm and 10±3 μm thick.

Since the evaluation on the formed electrodes was intended for conductivity (resistance), the evaluation was performed based on a current value in a state where a DC voltage (300 mV) was applied in air at 700° C. As for the evaluation, based on the measured current values, a case where the current value was less than 5 mA was designated as "x," a case where the current value was 5 mA or more but less than 5.5 mA was designated as "Δ," a case where the current value was 5.5 mA or more but less than 6 mA was designated as "○," and a case where the current value was 6 mA or more was designated as "⊙."

Further, in order to evaluate the electrode activity of each electrode, electrode resistance with respect to platinum weight per unit area was measured by an AC impedance method. The evaluation condition was as follows. A paste was printed on both side of a zirconia green sheet under the same condition as described above to prepare a processed and calcined electrode, and a current frequency response with respect to voltages with a frequency from 100 kHz to 100 mHz at an amplitude of 20 mV without DC bias in atmospheric atmosphere at 700° C. was measured. Then, the case of more than 20Ω was evaluated as "x," the case of more than 15Ω but 20Ω or less was evaluated as "Δ," the case of more than 10Ω but less than 15Ω was evaluated as "○," and the case of 10Ω or less was evaluated as "⊙." The evaluation results of these electrode characteristics are shown in Table 1.

TABLE 1

| Test No. | Conductive particle | Added amount of ceramic powder | Inorganic oxide particle Type | Particle diameter | Added amount | Insoluble particle Type | Particle diameter | Added amount | Electrode characteristics Conductivity | Electrode activity |
|---|---|---|---|---|---|---|---|---|---|---|
| 1 | Pt (0.7 μm) | 15 wt % | Al$_2$O$_3$ | 10 nm | 0.5 wt % | Acryl | 0.8 μm | 3.0 wt % | ○ | ○ |
| 2 | | | | | 1.1 wt % | | | | ⊙ | ⊙ |
| 3 | | | | | 2.3 wt % | | | | ⊙ | ⊙ |
| 4 | | | | | 3.0 wt % | | | | ○ | ○ |
| 5 | | | | | 2.3 wt % | | 0.1 μm | | Δ | ○ |
| 6 | | | | | | | 1.5 μm | | ⊙ | ⊙ |
| 7 | | | | | | | 0.8 μm | 1.0 wt % | ⊙ | ⊙ |
| 8 | | | | | | | | 2.0 wt % | ⊙ | ⊙ |
| 9 | | | | | | | | 4.0 wt % | ⊙ | ⊙ |
| 10 | | | — | — | 0 | | 0.1 μm | 3.0 wt % | X | X |
| 11 | | | | | | | 0.8 μm | | X | Δ |
| 12 | | | | | | | 1.5 μm | | X | X |

TABLE 1-continued

| Test No. | Conductive particle | Added amount of ceramic powder | Inorganic oxide particle Type | Particle diameter | Added amount | Insoluble particle Type | Particle diameter | Added amount | Electrode characteristics Conductivity | Electrode activity |
|---|---|---|---|---|---|---|---|---|---|---|
| 13 | | | Al₂O₃ | 10 nm | 2.3 wt % | — | — | 0 | X | X |
| 14 | | | — | — | 0 | — | — | 0 | X | X |
| 15 | | 10 wt % | Al₂O₃ | 10 nm | 2.3 wt% | Acryl | 0.8 μm | 3.0 wt % | ⊙ | ⊙ |
| 16 | | 15 wt % | | 200 nm | | | | | ⊙ | ⊙ |
| 17 | | | | 500 nm | | | | | ◯ | ⊙ |
| 18 | | | | 10 nm | | | 2.0 μm | | ⊙ | ⊙ |
| 19 | | | | | | | 3.0 μm | | ⊙ | ⊙ |
| 20 | | | | | | | | 5.0 wt % | ◯ | ◯ |
| 21 | | | MgO | 10 nm | 2.0 wt % | | 0.8 μm | 3.0 wt % | ⊙ | ⊙ |
| 22 | | | Al₂O₃ | 10 nm | 2.3 wt % | PE | 1.0 μm | | ⊙ | ⊙ |
| 23 | | | | | | PET | 1.2 μm | | ⊙ | ⊙ |
| 24 | | | Al₂O₃ | 200 nm | 0.5 wt % | Diamond | 0.8 μm | 10 wt % | ◯ | ◯ |
| 25 | | | | | 1.1 wt % | | | | ⊙ | ⊙ |
| 26 | | | | | 3.0 wt % | | | | ◯ | ◯ |
| 27 | | | Al₂O₃ | 200 nm | 2.3 wt % | Diamond | 0.8 μm | 5 wt % | ◯ | ◯ |
| 28 | | | | | | | | 8 wt % | ⊙ | ⊙ |
| 29 | | | | | | | | 10 wt % | ⊙ | ⊙ |
| 30 | | | | | | | | 13.5 wt % | ⊙ | ⊙ |
| 31 | | | | | | | | 15 wt % | ◯ | ⊙ |
| 32 | | | | | | | | 17.5 wt % | X | X |
| 33 | | | Al₂O₃ | 200 nm | 2.3 wt % | Diamond | 0.2 μm | 10 wt % | ◯ | Δ |
| 34 | | | | | | | 0.5 μm | | ⊙ | ⊙ |
| 35 | | | | | | | 1.4 μm | | ⊙ | ⊙ |
| 36 | | | Al₂O₃ | 200 nm | 2.3 wt % | Carbon | 3.0 μm | 5 wt % | ⊙ | ◯ |

First, from a study on the addition effect of the inorganic oxide particle and the insoluble particle, it can be confirmed from the comparison of Test No. 3 with Test Nos. 10 to 14 that favorable electrode characteristics are exhibited by adding both of the components to the metal paste. The electrode characteristics are not sufficient not only in a case where both of the inorganic oxide particle and the insoluble particle are not added, but also in a case where only one of them is added. Further, even when the particle diameter of the insoluble particle is adjusted as in Test Nos. 10 to 12, it is not possible to improve the electrode characteristics if the inorganic oxide particle is not added.

Regarding the added amount of the inorganic oxide particle in a range (0.5 to 3.0 mass %) studied in this embodiment, the electrode acts as an effective electrode (Test Nos. 1 to 4 and Nos. 24 to 26). It can be said that a preferable added amount is 1.1 to 2.3 mass %. Further, regarding the particle diameter of the inorganic oxide particle, with a range of 10 nm to 500 nm, a favorable result can be achieved (Test Nos. 3, 16, and 17). In addition, it is inferred from the result of Test No. 17 that, when the particle diameter exceeds 500 nm, the electrode characteristics may be adversely affected. Incidentally, as the inorganic oxide particle, in addition to alumina, magnesia is also applicable (Test No. 21).

Further, regarding the types of the insoluble particle, in addition to organic substances such as acryl, PE, and PET (Test Nos. 1 to 23), diamond and carbon were applicable (Test Nos. 24 to 36). In the case of using the organic substance, when the added amount thereof was 1.0 to 5.0 mass %, favorable electrode polarity was confirmed (Test Nos. 3, 7 to 9, and 20). Furthermore, in the case of using diamond or carbon, when the added amount was 1.0 to 15.0 mass %, favorable electrode characteristics were confirmed (Test Nos. 27 to 32, and 36).

Regarding the particle diameter of the insoluble particle, the insoluble particles having a particle diameter of 0.8 to 3.0 μm exhibited favorable characteristics (Test Nos. 3, 6, 18, 19, 34, and 35). However, in the case of the insoluble particles having a fine particle diameter of 0.2 μm or less, conductivity is slightly insufficient (Test Nos. 5 and 33). For this reason, the particle diameter is preferably larger than 0.2 μm.

Incidentally, regarding the ceramic powder, study on the added amounts of 10 mass % and 15 mass % was conducted in this embodiment, and both of the added amounts exhibited favorable results (Test Nos. 3 and 15).

Figure 3:
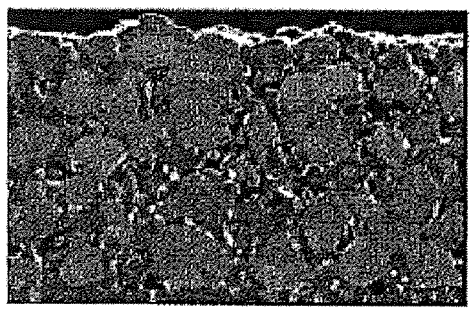
FIG. 3 is a cross sectional photograph and a surface photograph of an electrode produced in an embodiment of the present invention.
Figure 3:
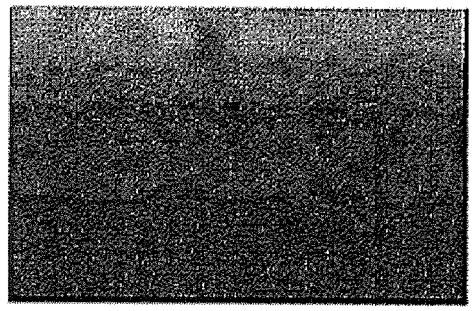

FIG. 3 shows results obtained when the cross section of the electrode produced in Test No. 3 and the cross section of the electrode produced in Test No. 14 are observed. As clearly seen from FIG. 3, the electrode produced in Test No. 3 has a porous structure having a large number of pores. Further, a state where a platinum particle (a white portion in the photograph) is not excessively sintered but is appropriately dispersed is shown. The electrode produced in Test No. 14 was dense with very few pores.

INDUSTRIAL APPLICABILITY

According to the present invention, a porous electrode film can be formed while the conductive metal and the ceramic powder are dispersed in a fine state. The present invention is preferably used as a metal paste for forming an oxygen sensor electrode or a sensor electrode of a gas sensor such as NOx sensor and can make the film thickness of an electrode film thin. Therefore, the present invention can lower costs of various sensor devices.

What is claimed is:

1. A metal paste for forming a gas sensor electrode, the metal paste consisting of a dispersion of:
   a) a conductive particle consisting of Pt or a Pt alloy,
   b) a ceramic powder consisting of zirconia or stabilized zirconia, or any of zirconia and stabilized zirconia and one or more oxides of La, Ce, Pr, Nd, Sm, and Hf in a solvent,
   c) an inorganic oxide particle consisting of alumina, and d) an insoluble particle that is insoluble in the solvent, wherein the insoluble particle is one or more selected from the group consisting of graphite and diamond powder, wherein 0.5 to 3.0 mass % of the inorganic oxide particle and 1.0 to 15.0 mass % of the insoluble particle are dispersed based on mass of solid content of the conductive particle, the ceramic powder, the inorganic oxide particle, and the insoluble particle to form the gas sensor electrode.

2. The metal paste for forming a gas sensor electrode according to claim 1, wherein the insoluble particle consists of diamond powder.

3. The metal paste for forming a gas sensor electrode according to claim 2, wherein 8.0 to 13.5 mass % of the insoluble particle is dispersed based on mass of solid content of the conductive particle, the ceramic powder, the inorganic oxide particle, and the insoluble particle to form the gas sensor electrode.

4. The metal paste for forming a gas sensor electrode according to claim 3, wherein a particle diameter of the insoluble particle is 0.5 to 1.4 µm.

5. The metal paste for forming a gas sensor electrode according to claim 4, wherein a particle diameter of the conductive particle is 5 nm to 2 µm.

6. The metal paste for forming a gas sensor electrode according to claim 4, wherein a particle diameter of the ceramic powder is 100 to 500 nm.

7. The metal paste for forming a gas sensor electrode according to claim 4, wherein a particle diameter of the inorganic oxide particle is 5 to 500 nm.

8. The metal paste for forming a gas sensor electrode according to claim 3, wherein a particle diameter of the conductive particle is 5 nm to 2 µm, a particle diameter of the ceramic powder is 100 to 500 nm, a particle diameter of the inorganic oxide particle is 5 to 500 nm, and a particle diameter of the insoluble particle is 0.5 to 1.4 µm.

9. The metal paste for forming a gas sensor electrode according to claim 4, wherein a particle diameter of the conductive particle is 5 nm to 2 µm, a particle diameter of the ceramic powder is 100 to 500 nm, and a particle diameter of the inorganic oxide particle is 5 to 500 nm.

10. The metal paste for forming a gas sensor electrode according to claim 1, wherein 5.0 to 15.0 mass % of the insoluble particle is dispersed based on mass of solid content of the conductive particle, the ceramic powder, the inorganic oxide particle, and the insoluble particle to form the gas sensor electrode.

11. The metal paste for forming a gas sensor electrode according to claim 1, wherein a dispersed amount of the ceramic powder is 10 to 20 mass % based on the mass of the solid content.

12. The metal paste for forming a gas sensor electrode according to claim 1, wherein the conductive particle comprises any of Pt and a Pt—Pd alloy containing 30 mass % or less of Pd.

13. The metal paste for forming a gas sensor electrode according to claim 1, wherein the solvent is one or more kinds of ethylene glycol, propylene glycol, ethylene glycol monophenyl ether, benzyl alcohol, kerosene, paraffin, γ-butyrolactone, N-methyl pyrrolidone, butyl carbitol, turpentine oil, α-terpineol, and terpineol.

14. The metal paste for forming a gas sensor electrode according to claim 1, wherein a particle diameter of the conductive particle is 5 nm to 2 µm.

15. The metal paste for forming a gas sensor electrode according to claim 1, wherein a particle diameter of the ceramic powder is 100 to 500 nm.

16. The metal paste for forming a gas sensor electrode according to claim 1, wherein a particle diameter of the inorganic oxide particle is 5 to 500 nm.

17. The metal paste for forming a gas sensor electrode according to claim 1, wherein a particle diameter of the insoluble particle is 0.5 to 3 µm.

18. The metal paste for forming a gas sensor electrode according to claim 1, wherein a particle diameter of the conductive particle is 5 nm to 2 µm, a particle diameter of the ceramic powder is 100 to 500 nm, a particle diameter of the inorganic oxide particle is 5 to 500 nm, and a particle diameter of the insoluble particle is 0.5 to 3 µm.

* * * * *